(12) United States Patent
Matsuura et al.

(10) Patent No.: US 8,080,370 B2
(45) Date of Patent: Dec. 20, 2011

(54) SCREENING METHOD FOR PROPHYLACTIC AND/OR THERAPEUTIC AGENT FOR DISEASE ACCOMPANIED BY HEPATITIS C

(75) Inventors: Yoshiharu Matsuura, Suita (JP); Kohji Moriishi, Suita (JP)

(73) Assignee: Osaka University, Suita-shi (JP)

( * ) Notice: Subject to any disclaimer, the term of this patent is extended or adjusted under 35 U.S.C. 154(b) by 86 days.

(21) Appl. No.: 12/311,333

(22) PCT Filed: Sep. 25, 2007

(86) PCT No.: PCT/JP2007/069155
§ 371 (c)(1),
(2), (4) Date: Mar. 26, 2009

(87) PCT Pub. No.: WO2008/041665
PCT Pub. Date: Apr. 10, 2008

(65) Prior Publication Data
US 2010/0297605 A1 Nov. 25, 2010

(30) Foreign Application Priority Data
Sep. 28, 2006 (JP) .................... 2006-266000

(51) Int. Cl.
*C12Q 1/70* (2006.01)
*C12Q 1/18* (2006.01)
*C12Q 1/68* (2006.01)
(52) U.S. Cl. .................. 435/5; 435/6.13; 435/32
(58) Field of Classification Search .................. None
See application file for complete search history.

(56) References Cited

FOREIGN PATENT DOCUMENTS
WO  WO-2006/021896 A2  3/2006

OTHER PUBLICATIONS

Wojcik (International Journal of Biochemistry & Cell Biology 1999:273-276, 1999).*
Moriishi et al (Journal of Virology 77:10237-10249, 2003).*
Moriishi et al (PNAS 104:1661-1666, 2007).*
Karimova et al (International Journal of Medical Microbiology 292:17-25, 2002).*
Yoshikawa et al (Journal of Biological Chemistry 277:1705-1711, 2002).*
Matsuura et al (The Japanese Cancer Association Gakujutsu Shokai Kiji, 65, Aug. 2006, p. 75).*
Kyoji Moriya et al., "The core protein of hepatitis C virus induces hepatocellular carcinoma in transgenic mice," Nature Medicine 4, 1998, pp. 1065-1067.
L.-R. You et al., "Hepatitis C Virus Core Protein Interacts with Cellular Putative RNA Helicase," J. Virol. 73: 1999, pp. 2841-2853.
M. Otsuka et al., "Hepatitis C Virus Core Protein Enhances p53 Function through Augmentation of DNA Binding Affinity and Transcriptional Ability," J. Biol. Chem. 275: 2000, pp. 34122-34130.
T. Yoshida et al., "Activation of STAT3 by the Hepatitis C Virus Core Protein leads to Cellular Transformation," J. Exp. Med. 196: 2002, pp. 641-653.
K. Moriishi et al., "Proteasome Activator PA28γ-Dependent Nuclear Retention and Degradation of Hepatitis C Virus Core Protein," J. Virol., 77, 19, 2003, pp. 10237-10249.
D-Y Jin et al., "Hepatitis C virus core protein-induced loss of LZIP function correlates with cellular transformation," EMBO J. 19: 2000, pp. 729-740.
A. Alisi et al., "Physical and functional interaction between HCV core protein and the different p73 isoforms," Oncogene 22(17): 2003, pp. 2573-2580.
K. Watashi et al., "Modulation of Retinoid Signaling by a Cytoplasmic Viral Protein via Sequestration of Sp110b, a Potent Transcriptional Corepressor of Retinoic Acid Receptor, from the Nucleus," Mol. Cell Biol. 23(21): 2003, pp. 7498-7509.
M. Gomez-Gonzalo et al., "Hepatitis C virus core protein regulates p300/CBP co-activation function. Possible role in the regulation of NF-AT1 transcriptional activity," Virology 328(1): 2004, pp. 120-30.
R-T Mai et al., "Hepatitis C virus core protein recruits nucleolar phosphoprotein B23 and coactivator p300 to relieve the repression effect of transcriptional factor YY1 on B23 gene expression," Oncogene Jan. 19; 25 (3): 2006, pp. 448-462.
Y. Matsuura et al., "Critical role of PA28gamma in hepatitis C virus-associated steatogenesis and hepatocarcinogenesis," The Japanese Cancer Association Gakujutsu Shokai Kiji, 65, 2006, 2 sheets including p. 75.
K. Moriishi et al., Proteasome activator PA28γ-dependent nuclear retention and degradation of hepatitis C virus core protein. J. Virol, 77, 2003, pp. 10237-10249.
M. Rechsteiner et al., "Mobilizing the proteolytic machine: cell biological roles of proteasome activators and inhibitors," Trends in Cell Biology, 15, 2003, pp. 27-33.
K. Moriishi et al., "Critical role of PA28γ in hepatitis C virus-associated steatogenesis and hepatocarcinogenesis," Proc. Natl. Acad. Sci. USA, 104, 2007, pp. 1661-1666.
International Search Report mailed Dec. 25, 2007, issued on PCT/JP20071069155.
Natalia A. Osna et al., "Hepatitis C virus core protein activates proteasome function by induction of oxidative stress in liver cells," Hepatology, vol. 44, No. 4, Suppl. 1, Oct. 2006, p. 584A.
Supplementary Partial European Search Report dated Mar. 26, 2010, issued on the European patent application No. 07828895.8.

* cited by examiner

*Primary Examiner* — Mary E Mosher
(74) *Attorney, Agent, or Firm* — Edwards Wildman Palmer LLP

(57) ABSTRACT

An easy and efficient screening method for an agent useful for prevention and/or treatment of hepatitis C virus-related disease, and a prophylactic and/or therapeutic agent for hepatitis C virus-related disease obtained by the method. The screening method comprises a step of examining the inhibitory activity of an test substance on the protein-protein interaction between hepatitis C virus core protein and PA28.gamma,. The method can be carried out by using transcriptional activity of a lipid metabolism-control factor as indicator. The test substance used in the method may have an activity to inhibit expression or function of the PA28.gamma. gene. The hepatitis C virus-related diseases include fatty liver, acute hepatitis, chronic hepatitis, liver cirrhosis, liver cancer, and insulin-resistant diseases. The method is extremely useful as a method of obtaining an agent superior in preventive and therapeutic activity particularly to diseases such as fatty liver and liver cancer.

1 Claim, 5 Drawing Sheets

Fig. 5
(I) SREBP-1c
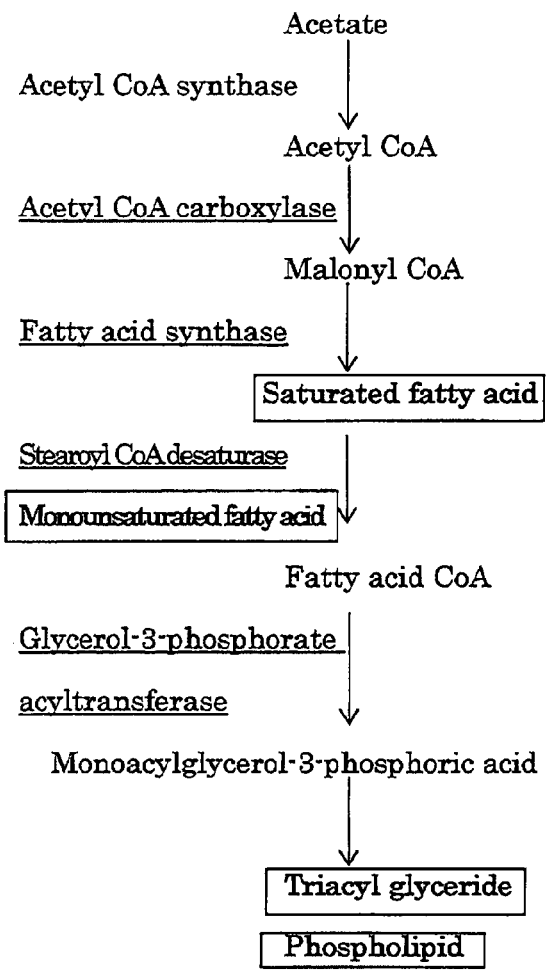
(II) SREBP-2
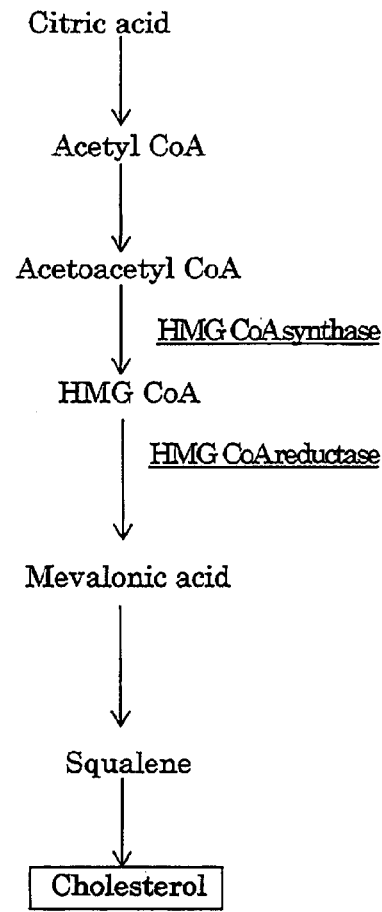

SCREENING METHOD FOR PROPHYLACTIC AND/OR THERAPEUTIC AGENT FOR DISEASE ACCOMPANIED BY HEPATITIS C

TECHNICAL FIELD

The present invention relates to a method for screening prophylactic and/or therapeutic agents for diseases accompanied by hepatitis C such as fatty liver, liver cancer and the like, and prophylactic and/or therapeutic agents obtained by the method.

BACKGROUND ART

Hepatitis C virus (HCV) has a single-stranded positive-sense RNA as the gene. The large precursor protein translated from the HCV RNA having approximately 3000 amino acids is cleaved by host cell- and virus-derived proteases into a core protein and two envelope proteins, that constitute the virus particle, and other non-structural proteins.

The core protein, which constitutes the virus particle, is also known to migrate into the nucleus of host cell. Recently, it has been reported that the core protein is deeply involved in development of liver cancer through regulating the functions of the host cell in various ways. Nature Medicine 4, 1065-1067(1998), for example, describes that a transgenic mouse expressing the HCV core protein develops, via fatty liver, liver cancer at high incidence rate. Since then, for the purpose of elucidating the molecular mechanism of development of liver cancer by the core protein, the methods of identifying host proteins that interact with the core protein and analyzing the functions of the proteins have intensively studied. There have been many reported host proteins interacting with the core proteins, such as p53 [J. Biol. Chem. 275: 34122-34130 (2000)], RNA helicase [J. Virol. 73: 2841-2853(1999)], STAT 3 [J. Exp. Med. 196: 641-653 (2002)], PA28y [J. Virol., 77, 19, 10237-10249 (2003)], LZIP [EMBO J. 19: 729-740 (2000)], P73 [Oncogene 22(17): 2573-80 (2003)], Sp110b [Mol. Cell Biol. 23 (21): 7498-509 (2003)], P300/CBP [Virology 328(1): 120-30 (2004)], and B23 [Oncogene Jan 19; 25(3): 448-62 (2006)].

J. Biol. Chem. 275: 34122-34130 (2000) reports that the core protein, in interaction with the p53 C-terminal region, increases and strengthens the p53 transcriptional activity via increasing the DNA-binding affinity of p53. J. Virol. 73: 2841-2853(1999) describes that the cellular RNA helicase, which is originally localized in the nucleus, becomes co-localized in the cytoplasm due to interaction with the N-terminal 40 amino acids of the HCV core protein. However, there is no direct evidence of in-vivo interaction between the core protein, and the host proteins p53 and RNA helicase, and also the other host proteins such as LZIP, P73, Sp110b, P300/CBP and B23.

J. Exp. Med. 196: 641-653 (2002) discloses that the core protein binds to STAT3 directly and activates STAT3 by phosphorylation via a JAK-independent pathway. The same document reports that a cell forcibly expressing the HCV core protein and STAT3 exhibits anchorage-independent growth and tumor formation. J. Virol., 77,19,10237-10249 (2003) discloses that the core protein interacts with PA28γ to be localized in the nucleus. PA28γ is known to be a proteasome-regulating protein localized in cell nucleus, that interacts with 20S proteasome to increase its peptidase activity. The document also reports that the 44 to 71 amino acid region of the core protein is involved both in binding with PA28γ and intranuclear localization and that the core protein is susceptible to PA28γ-dependent decomposition.

However in any document, there was no sufficient data directly showing relationship between the core protein and liver cancer, and the specific mechanism of involved in development of liver cancer not yet fully is elusidated.

Nonpatent Document 1: Nature Medicine 4, 1065-1067 (1998)
Nonpatent Document 2: J. Virol. 73: 2841-2853(1999)
Nonpatent Document 3: J. Biol. Chem. 275. 34122-34130 (2000)
Nonpatent Document 4: J. Exp. Med. 196: 641-653 (2002)
Nonpatent Document 5: J. Virol., 77, 19, 10237-10249 (2003)
Nonpatent Document 6: EMBO J. 19: 729-740 (2000)
Nonpatent Document 7: Oncogene 22(17): 2573-80 (2003)
Nonpatent Document 8: Mol. Cell Biol. 23(21): 7498-509 (2003)
Nonpatent Document 9: Virology 328(1): 120-30 (2004)
Nonpatent Document 10: Oncogene Jan 19; 25 (3): 448-62(2006)

SUMMARY OF THE INVENTION

Problems to be Solved by the Invention

An object of the present invention is to provide a screening method allowing easy and efficient identification of an agent useful for prevention and/or treatment of hepatitis C virus-related diseases and to provide a prophylactic and/or therapeutic agent for hepatitis C virus-related diseases obtained by the method.

Means to Solve the Problems

After intensive studies to achieve the object, the inventors have found that it was possible to inhibit progress of the symptoms of the diseases associated with hepatitis C such as fatty liver and liver cirrhosis and thus, to reduces the incidence rate of liver cancer significantly through regulation of lipid metabolism by inhibiting the interaction between the hepatitis C virus core protein and PA28γ, and completed the present invention.

Specifically, the present invention relates to a screening method for a prophylactic and/or therapeutic agent for at least one disease associated with hepatitis C selected from fatty liver, liver cirrhosis and liver cancer, comprising a step of examining the inhibitory activity of an test substance on the protein-protein interaction between the hepatitis C virus core protein and PA28γ (hereinafter, referred to simply as the "method 1 according to the present invention"). The inhibitory activity on the protein-protein interaction may be examined by using the transcriptional activity of lipid metabolism-control factors as an indicator or by using the inhibitory activity on expression or function of the PA28γ gene as an indicator.

The present invention also provides a prophylactic and/or therapeutic agent for at least one hepatitis C-related disease selected from fatty liver, liver cirrhosis and liver cancer, containing the substance obtained by the screening method according to the present invention as an active ingredient (hereinafter, referred to simply as the "prophylactic and/or therapeutic agent according to the present invention"). The substance inhibiting the protein-protein interaction may be a substance having an activity to inhibit expression or function of the PA28γ gene.

The present invention still provides a screening method for a lipid synthesis inhibitor, including a step of examining the inhibitory activity of an test substance on the protein-protein interaction between the hepatitis C virus core protein and PA28γ (hereinafter, referred to simply as the "method 2 according to the present invention"). The inhibitory activity on the protein-protein interaction is examined by using expression of a reporter gene connected to the region under control of the promoter for the lipid metabolism-control factor, and the lipid metabolism-control factor used may be SREBP-1c.

The present invention provides a lipid synthesis inhibitor, including the substance obtained by the method according to the present invention as an active ingredient. The lipid synthesis inhibitor according to the present invention may contain a substance having an activity to inhibit expression or function of the PA28γ gene as an active ingredient.

ADVANTAGEOUS EFFECTS OF THE INVENTION

According to the method of the present invention, it is possible, by examining the activity to inhibit interaction between the hepatitis C virus-derived core protein and the host-derived PA28γ, to efficiently identify a substance capable of controlling expression of lipid synthases via modification of transcriptional activity, for example, that of lipid metabolism-control factors induced by the interaction. The substance thus obtained can be used as an active ingredient in lipid synthesis inhibitor, and, in particular, it is useful as an active ingredient in prophylactic and/or therapeutic agent for prevention of development of diseases associated with hepatitis C such as fatty liver, liver cirrhosis, and liver cancer and for suppressing progress of the symptoms thereof. The prophylactic and/or therapeutic agent according to the present invention may be administered therapeutically effectively to the patients with developed hepatitis C virus-related diseases and also to the HCV carrier patients before development of the diseases as a prophylactic agent for preventing development of the HCV-related diseases.

BRIEF DESCRIPTION OF THE DRAWINGS

FIG. 1b is an electrophoretic photograph of a PCR amplification product used in genotyping. FIG. 1c is a Western blotting image for analysis of the proteins expressed in the mouse liver tissue. FIG. 1d shows as for the body weight of the 6 months old mice, there was no significant difference among PA28γ$^{+/+}$, PA28γ$^{+/+}$ core Tg, PA28γ$^{-/-}$ core Tg, and PA28γ$^{-/-}$ mice. FIG. 1e shows that the expression amount of the core protein was higher in male mice than in female mice, both in PA28γ$^{+/+}$ core Tg mice and PA28γ$^{-/-}$ core Tg mice.

FIGS. 3(A) to 3(D) show the transcription amounts of the genes respectively coding SREBP-1a (A), SREBP-1c (B), SREBP-2(C) and stearoyl CoA desaturase (D) in the liver of mice of 2 months of age, while FIGS. 3(E) to 3(J) show the transcription amounts of the genes respectively coding SREBP-1c (E), fatty acid synthase (F), acetyl CoA carboxylase (G), stearoyl CoA desaturase (H), HMG CoA reductase (I), and HMG CoA synthase (J) in the liver of mice of 6 months of age, as expressed as relative values to the transcription amount of HPRT.

FIG. 4(a) is a schematic view illustrating the principle of the assay; FIG. 4(b) includes graphs showing the reporter activity for the combination of the genes expressed in PA28γ$^{+/+}$ MEF cell (left) or PA28γ$^{-/-}$ MEF cell (right); FIG. 4(c) is a graph showing the reporter activity observed when corresponding ligands are added to the HEK293T cell in which the combination of the core protein, LXRα and RXRα are expressed exogenously; and FIG. 4(d) is a graph comparing the reporter activities of core protein and mutant core protein lacking the C-terminal region.

FIG. 5(I) is a flow chart showing the lipid synthesis-control route by SREBP-1c, while FIG. 5(II) is a flow chart showing the lipid synthesis-control route by SREBP-2.

BEST MODE OF CARRYING OUT THE INVENTION

Figure 1:
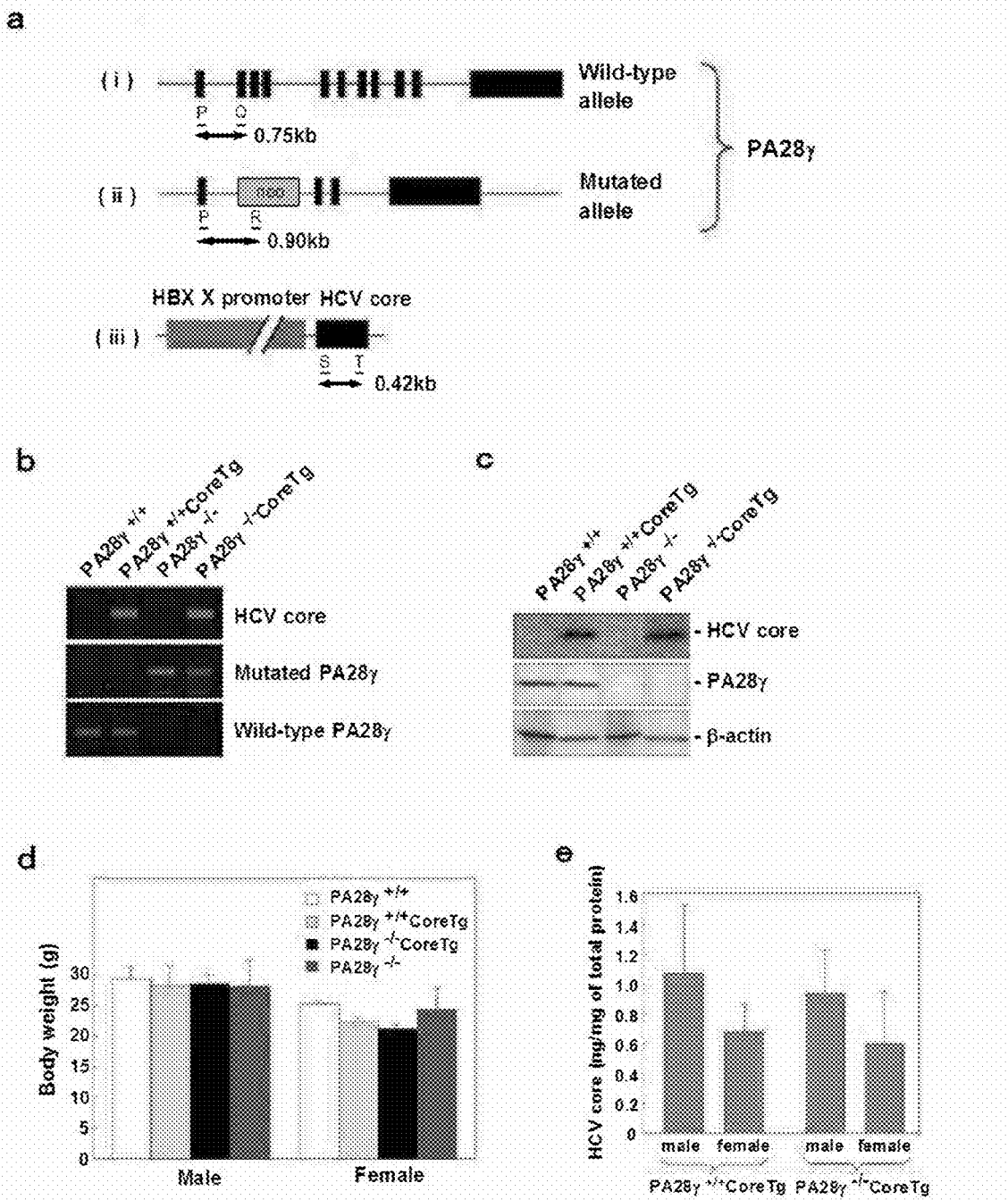
FIG. 1 is a schematic view showing the sequence structures of the genotype-specific genes on the chromosome of the mouse used in Example 1: FIGS.:1a (i): wild-type (PA28 γ$^{+/+}$); (ii): mutant PA28γ(PA28γ$^{-/-}$); and (iii): HCV core protein-incorporated type (core Tg).

The method 1 according to the present invention is characterized by including a step of examining the inhibitory activity of the test substance on the interaction between the hepatitis C virus core protein and PA28γ.

The hepatitis C virus (HCV) core protein is a structural protein formed by decomposition of a large precursor protein translated from hepatitis C virus RNA. The amino acid sequence of the HCV core protein and the base sequence coding the protein are known, and its amino acid sequence is, for example, the sequence of Swiss-Prot accession No. P26662. The HCV core protein for use in the screening method according to the present invention is not limited to the wild-type protein represented by the sequence above, and may be, for example, a mutant protein having a mutant sequence, in which some of the amino acids in the wild-type protein are deleted, or they are replaced with non-wild type amino acid, or other amino acid residue(s) or sequence(s) is/are added to the wild-type protein, so long as the protein can induce development of a HCV-related disease. Such a mutant protein is, for example, a mutant protein at least having activity to interact with PA28γ or nuclear localization activity, and the like, and specific examples thereof include proteins containing at least the 44 a.a. to 71 a.a. region of the wild-type amino acid sequence and the like. The HCV core protein may be a hepatitis C virus-derived natural protein or a synthetic protein, or alternatively, may be a protein obtained by expression in cell by using a recombinant vector incorporating a base sequence coding the protein.

PA28γ is a nuclear localization protein known as a proteasome-regulating protein that binds to the HCV core protein specifically and accelerates decomposition of the protein in the nucleus. The amino acid sequence of PA28γ and the base sequence coding the protein are known, and for example, known is a human-derived PA28γ having the amino acid sequence of Swiss-Prot accession number P61289. In addition of human homologue, There are many homologues of PA28γ, such as those of simian, mouse, swine and others, and these amino acid sequences are disclosed in Swiss-Prot and can be used as a PA28γ in the present invention, similarly to the PA28γ above. The PA28γ for use in the screening method according to the present invention is not limited to the wild-type protein represented by the sequence above, and maybe, for example, a mutant protein having a mutant sequence, in which some of the amino acids in the wild-type protein are deleted, or they are replaced with non-wild type amino acid, or other amino acid residue(s) or sequence is/are added to the wild-type protein, so long as the protein induces a HCV-related disease. For example, a mutant protein at least having an activity to regulate proteasome or migrate into the nucleus may be used as the mutant protein.

The interaction between virus-derived HCV core protein and host-derived PA28γ has been considered to be required in development of HCV-related diseases and the initial phase of various symptoms thereof, but the mechanism was yet to be understood. In contrast, the inventors had already reported that HCV core proteins lacking the interaction region with PA28γ or the lack of PA28γ led to the migration out of the nucleus into the cytoplasm and that excessive expression of PA28γ resulted in acceleration of protein decomposition of the core protein. After additional studies, the inventors have found that deficiency of PA28γ led to accumulation of the core protein in the nucleus and inhibition of the development and progress of the diseases associated with hepatitis C such as fatty liver, liver cirrhosis and liver cancer, and concluded that the inhibition of the interaction between the virus-derived HCV core protein and the host-derived PA28γ can result in prevention of development of the HCV-related disease of HCV-infected patients and allows to result in delay or blockage of the progress of the symptoms of the patients already with the disease. The present invention was made based on these findings. Specifically, the method 1 according to the present invention is a method for screening prophylactic and/or therapeutic agents for at least one disease associated with hepatitis C selected from fatty liver, liver cirrhosis, and liver cancer.

The test substance for use in the method 1 according to the present invention may be any known or novel compound, and examples thereof include synthetic or natural organic compounds such as nucleic acids, carbohydrates, lipids, protein, peptides and organic low-molecular compounds, and the like.

In the present invention, the inhibitory activity to the protein-protein interaction between the hepatitis C virus core protein and PA28γ can be evaluated either in vivo or in vitro, and for example, it may be detected directly by a method of detecting the signal such as fluorescence by the interaction in vitro with a labeled protein or indirectly by a method of detecting various biological activities induced by the protein-protein interaction in a cell as an indicator. The latter method is particularly favorable in the present invention, and in particular a method of evaluating the transcriptional activity of a lipid metabolism-control factor as indicator is preferable, as will be described below. Also preferably used in the present invention is a method of measuring the inhibitory activity on the protein-protein interaction, by using the inhibitory activity on expression or function of PA28γ gene as indicator.

In-vivo methods for detection of interaction inside a cell include, for example, methods of using a prokaryotic or eukaryotic host cell such as yeast two hybrid system and reporter assay system. In-vitro methods for detection of protein-protein interaction include methods of using a purified protein labelled for example with a fluorescence or radiation ray label and the like. In-vivo methods of detecting protein-protein interaction inside a cell, especially reporter assays, are preferable because they are superior in reproducibility of the virus-infected state and simpler in operation.

In the reporter assay use, for example, an evaluation method of using, as an indicator, expression of a reporter gene that is bound to the region under control of the promoter region for the genes, transcription of which is directly or indirectly under control driven by the interaction between the HCV core protein and PA28γ. Favorable examples of the useful promoter regions connected to the reporter genes include promoter regions for lipid metabolism-control factors, preferably promoter regions for the genes coding sterol regulatory element binding proteins (SREBPs) such as SREBP-1c and SREBP-2. The transcriptional activity (promoter activity) of these lipid metabolism-control factors is known to regulate lipid synthesis by expression control of lipid synthase.

For example as shown in FIG. 5(I), SREBP-1c can regulate lipid synthesis by expression control of lipid synthases. As shown in FIG. 5(I), SREBP-1c regulates synthesis of lipids comprising saturated fatty acids, monounsaturated fatty acids, triglycerides and phospholipids, by expression control of lipid synthases such as acetyl CoA carboxylase, fatty acid synthase and stearoyl CoA desaturase. FIG. 5(II) is a flow-chart showing the similar route by SREBP-2, and specifically, SREBP-2 regulates synthesis of lipids comprising saturated fatty acids, monounsaturated fatty acids, triglycerides and phospholipids, by expression control of lipid metabolism-control factors such as HMG CoA synthase and HMG CoA reductase and lipid metabolism-control factors comprising fatty acid synthase and stearoyl CoA desaturase.

As described above, the transcriptional activity of the lipid metabolism-control factor can control lipid synthesis. Therefore, the method of evaluating the inhibitory activity on the protein-protein interaction by using transcription of the lipid metabolism-control factor as indicator would be useful in screening a substance effective for prevention and treatment of lipid accumulation-derived diseases such as fatty liver wherein the method is based on the regulation of cholesterol synthesis. Thus in the present invention, it is possible by using the screening method to obtain a lipid synthesis inhibitor containing a substance inhibiting the interaction between the hepatitis C virus core protein and PA28γ as an active ingredient. The substance used as the active ingredient preferably has an activity to inhibit expression or function of the PA28γ gene.

The reporter gene is not particularly limited, and any known gene may be used, but a luciferase such as firefly luciferase or *Renilla* luciferase is used preferably because it is superior in detection sensitivity and convenience in handling. In the present invention, a dual luciferase reporter assay method of using firefly and *Renilla* luciferases in combination is used favorably because it is superior in reproducibility and gives high-reliability results.

Known or conventional expression vectors, cells and others properly selected according to the screening method are used in the screening method according to the present invention. Specifically, in the case of a yeast two hybrid system, pGBKT7, pACT2, GADT7 or the like may be used as the expression vector, and *Saccharomyces cerevisiae* AH109 or the like may be used as the cell. In the case of reporter assay, pGL3 (Promega Corporation) for example is used as the expression vector because of its excellent transformation efficiency; and an established cell line such as mouse embryonic fibroblast (MEFs) or human embryonic kidney cell (HEK293) or a living cell from a liver of HCV-infected animal is used favorably as the cell, because of its favorable transformation efficiency. In particular, for example, a PA28γ-producing cell such as human embryonic kidney cell (HEK293T) or liver cell is preferable, in light of its preferable reproducibility of HCV infection.

Transformation can be performed by using a recombinant vector carrying an expression vector containing a desired sequence according to the kind of cell described above by a known method properly selected. The transformant obtained can be cultivated under common culture condition, by using a known medium suitable for the kind of the cell.

Preferred embodiments of the methods (1 and 2) according to the present invention include a reporter assay method using a lipid metabolism-control factor present in the SREBP-1c promoter region and the like.

Transcription of SREBP-1c has been known to be activated, when a complex of liver X receptor (LXR) and retinoid X receptor (RXR) belonging to nuclear hormone receptor family (RXRα/LXRα complex) binds to the promoter region. The RXRα/LXRα-dependent transcription is activated by coexpression of the HCV core protein. The detailed mechanism is not completely understood, but a generally accepted model is that release of RXRα/LXRα heterodimer coinhibitor (such as Sp110b) into the cytoplasm in interaction (binding) with the HCV core protein activates transcription of SREBP-1c. The screening method is based on the phenomenon of the transcriptional activity of the SREBP-1c promoter region being controlled by the interaction between the HCV core protein and PA28γ.

The reporter assay method by using the SREBP-1c promoter region may adapt, for example, a method of transforming a cell by using an expression vector having a reporter gene introduced as it is expressible under control of the SREBP-1c promoter region and one or more recombinant vectors carrying genes coding HCV core protein, and proteins of PA28γ, RXRα and LXRα expressibly introduced, cultivating the obtained transformant in a medium containing 9-cis-retinoic acid (9cisRA: ligand for RXRα) and 22(R)-hydroxycholesterol (22(R)HC: ligand for LXRα) in the presence of or in the absence of the test substance, and evaluating the reporter activity in the resulting cultivates. The test substance may be added as it is or together with a recombinant vector or a known carrier depending on the type of the test substance.

The test substance evaluated by the method above to have an activity to inhibit the interaction between the hepatitis C virus core protein and PA28γ preferably has an activity to inhibit expression or function of the PA28γ gene. Such a substance seems to exhibit further more preferable preventive and therapeutic action, by blocking the PA28γ-dependent proteasome route and accumulating the HCV core protein in the nucleus without decomposition thereof, and consequently, inhibiting transcription for example of the disease-related factors.

It is possible by the screening method according to the present invention to obtain at high efficiency a medicine superior in inhibiting development of fatty liver, liver cancer, or the like and suppressing progress of the symptoms of the HCV-related diseases in the host after infection with hepatitis C virus. In particular, the screening method according to the present invention can be used as a simple and easy screening method for screening a substance useful as a lipid synthesis inhibitor by using the transcriptional activity of a lipid metabolism-control factor as indicator.

The method for confirming the preventive and/or therapeutic effect on a hepatitis C virus-related disease used in the present invention is, for example, a method of confirming suppression effect on transcription of a lipid metabolism-control factor by using the reporter assay method described above, or a method for confirming decrease in the amount of lipid accumulation in liver cell and in the incidence of liver cancer by comparing an animal infected with HCV or a non-human animal with a transduced gene coding the HCV core protein in the expressible form via gene modification (e.g., HCV core Tg mouse) with administering an test substance, with an non-administered animal.

The prophylactic and/or therapeutic agent for hepatitis C virus-related disease according to the present invention (hereinafter, referred to simply as the "HCV therapeutic agent according to the present invention") contains a substance inhibiting the interaction between the hepatitis C virus core protein and PA28γ as the active ingredient. The substance inhibiting the protein-protein interaction is not particularly limited, if it is a substance inhibiting or blocking the interaction between the hepatitis C virus core protein and PA28γ. Such a substance shows preventive and therapeutic effects, through inhibitory activity on the interaction, for example by regulating transcription or translation of the factors that induce development of HCV-related diseases and progress of their symptoms. The substance inhibiting the protein-protein interaction can be obtained, for example, by using the screening method according to the present invention.

The HCV therapeutic agent according to the present invention preferably has an activity to inhibit expression or function of the PA28γ gene. As used herein, the term "expression" means that a protein is being produced, and the term "inhibitory activity on expression" may be an effect in any phases including gene transcription, post-transcriptional regulation, translation to protein, post-translational modification, protein folding and the like. The substance having the "inhibitory activity on expression" may be a substance decreasing or suppressing signal transmission by acting on a functional site such as the protein-protein interaction site or active site in protein, a dominant negative mutant of a protein interacting with PA28γ or the core protein, or the like. The "dominant negative mutant" is a mutant lower in biological activity formed by introduction of mutation(s) in protein (e.g., deletion of functional region). These mutants can inhibit the function indirectly by competing with the wild-type equivalent.

Examples of the substances inhibiting expression of PA28γ include transcription-suppressor, RNA polymerase inhibitors, protein synthesis inhibitors, protein-decomposing enzymes, protein-denaturing agent modifying agents, splicing or mRNA cytoplasm migration-inhibiting factors, mRNAases, mRNA-inactivating factors by binding to the mRNA and the like, but substances specifically acting to the target molecule are preferable for minimizing the adverse reactions on other genes and proteins. Preferable examples of the substances inhibiting expression of PA28γ specifically include PA28γ or the equivalences thereof; functional nucleic acids such as siRNA, shRNA, miRNA, ribozymes, antisense nucleic acids, aptamers, decoy nucleic acids and the like; and functional proteins such as antibodies. These functional nucleic acids and proteins may be those produced in the administered subject after administration or may be produced by a known method, for example, by using expression vector, cell, and the like as needed. Functional nucleic acids are preferable because they afford specificity to the target molecule provided if needed and are superior in convenience in handling, and especially, aptamers, antisense nucleic acids, siRNAs and the like are used preferably. If a functional nucleic acid is used, nucleotide is used having the length of the region complementary to or the same as that of the target molecule, for example, 15 to 30 bases, preferably 18 to 25 bases, more preferably approximately 20 to 23 bases.

The prophylactic and/or therapeutic agent for hepatitis C virus-related diseases containing the substance inhibiting the protein-protein interaction as active ingredient is administered orally or parenterally, for example, as it is dissolved or suspended in a suitable vehicle. Examples of the parenteral administration include systemic administration such as intravenous, intraarterial, intramuscular, intraperitoneal and intratracheal administration and the like and topical administration to liver or the region in the vicinity of liver, but are not limited thereto. In particular, oral administration is preferable.

The HCV therapeutic agent according to the present invention is preferably included in a drug delivery system designed to deliver the substance inhibiting the protein-protein interaction reliably to the liver or the cells in the vicinity of liver, allow penetration thereof through cell membrane, and accelerate release of the agent from lysosome and endosome. For improvement of nuclease resistance, intracellular migration and release of the agent from lysosome/endosome, a method of modifying the functional nucleic acid or protein chemically in various ways may be used, and, for example in the case of an oligonucleic acid molecule such as antisense nucleic acid, a known method, for example a chemical modification method, such as modification of the phosphate bond or the saccharide region, or use of a morphine skeleton-containing oligonucleic acid, PNA or the like replacing the phosphate skeleton, may be used.

The formulation may be liquid or solid, and, examples of the formulations include liquids containing an effective amount of inhibitor dissolved, dispersed, or emulsified in a dilute solution or dispersion medium such as water or physiological saline; solid formulations, such as capsule, sachet and tablet, containing an effective amount of inhibitor as solid or granule; and the like.

The HCV therapeutic agent according to the present invention may contain the active ingredient, i.e., the substance inhibiting the protein-protein interaction, as it is or alternatively, as it is contained in an microcapsule preparation, as enclosed in liposome or a sustained-release material, or in a support, as supported on a carrier. Advantageously, encapsulation, for example in liposome, protects the active ingredient from decomposition by nuclease or protease and facilitates delivery of the agent into cell by endocytosis caused by binding of the liposome membrane to the cell surface. Encapsulation in a sustained-release material such as collagen assures long-term preservation of the active ingredient.

The HCV therapeutic agent according to the present invention may contain known pharmaceutically allowable additives, in addition to the ingredients above.

The dosage of the HCV therapeutic agent varies according to the kinds of the effective ingredients used for the agent, the administration method, the symptoms, the kinds and the sizes of the objects to be administered, the pharmaceutical properties and the like, but normally, the daily adult dosage of the active ingredient is, for example, approximately 0.0001 to 10 mg/kg, preferably approximately 0.0005 to 5 mg/kg, and may be administered once or multiple times a day.

The lipid synthesis inhibitor according to the present invention contains a substance inhibiting the interaction between the hepatitis C virus core protein and PA28γ as the active ingredient. Such a substance can be selected, for example, by the screening method according to the present invention, and in particular, a reporter assay method of using the transcriptional activity of a lipid metabolism-control factor as the indicator is used preferably.

The present invention provide in a simple and easy method of obtaining a substance having an activity to inhibit the interaction between the hepatitis C virus-derived core protein and the host-derived PA28γ and to suppress transcription of the lipid metabolism-control factor and others induced by the interaction. Such a substance inhibits or blocks lipid accumulation, and shows an excellent preventive and therapeutic effect on hepatitis C virus-related diseases such as fatty liver and liver cancer.

EXAMPLES

Hereinafter, the present invention will be described more in detail with reference to Examples, but it should be understood that the present invention is not restricted by these Examples.

Example 1

Preparation of PA28γ knockout mouse containing HCV core transgene (1) Preparation of Plasmid PA28γ cDNA was isolated from human fetal brain library (K. Moriishi et al., J. Virol. 77, 10237 (2003)). The HCV protein was amplified from HCV strain J1 (genotype 1b; H. Aizaki et al., Hepatology 27, 621 (1998)) and cloned into pCAG-C-S (H. Niwa, K. Yamamura, J. Miyazaki, Gene 108, 193 (1991)). Mouse cDNAs, RXRα and RXRα, were amplified by PCR from mouse liver total cDNA. The RXRα and RXRα genes obtained were respectively incorporated into pEFFlagGspGBK (D. C. Huang, S. Cory, A. Strasser, Oncogene 14, 405 (1997)) and pcDNA3.1 (manufactured by Invitrogen Corporation). The mouse anti-Flag (M2) antibody and the mouse anti-β-actin antibody used were products of Sigma Corporation; the rabbit polyclonal antibody to the synthesis peptide corresponding to the 70 to 85 amino acids of PA28γ was a product of Affinity Co., Ltd.; and the horseradish peroxidase-bound goat anti-mouse IgG and the anti-rabbit IgG were products of ICN Pharmaceuticals. The rabbit anti-HCV core protein was prepared, according to the method described in R. Suzuki et al., J. Virol. 79, 1271 (2005), by immunization with a recombinant HCV core protein (1 to 71 amino acid sequence). The mouse monoclonal antibody to the HCV core protein was the antibody described in K. Aoyagi et al., J. Clin. Microbiol 37, 1802 (1999) that was provided.

(2) Preparation of PA28γ Knockout Mouse Containing HCV Core Transgene

The C57BL/6 mouse strain 49 having a gene coding the HCV strain J1 genotype 1b (core Tg) and its PA28γ$^{-/-}$ mouse were prepared according to the methods described in K. Moriya et al., J. Gen. Virol. 78, 1527 (1997), and S. Murata et al., J. Biol. Chem. 274, 38211 (1999). These regions characteristic in mouse chromosome are shown in FIGS. 1a(i) to (iii). (i) represents a wild-type gene (PA28γ$^{+/+}$); (ii) represents a mutant PA28γ gene (PA28γ$^{-/-}$) lacking the function of the PA28γ gene, prepared by replacing the exons 2 to 8 in the PA28γ gene with a marker gene (neo); and (iii) represents a HCV core protein-containing-type gene (core Tg) containing a gene coding the HCV core protein introduced in the region under control of HBV X promoter, respectively. Mouse genotyping was performed by PCR analysis of genomic DNA extracted from the mouse tail, by using two primers (P and Q) from the wild-type (PA28γ$^{+/+}$) gene amplifying the 0.75 kb DNA, two primers (P and R) amplifying the 0.90 kb DNA containing part of the marker gene introduced from the mutant (PA28γ$^{-/-}$), and additionally, two primers (S and T) amplifying the 0.42 kb DNA containing the gene coding the HCV core protein introduced from the mutant (core Tg), respectively.

The PA28γ$^{-/-}$ mouse and the core Tg mouse were mated with each other; and, then, the littermate PA28γ$^{+/-}$ core Tg mice thus obtained were mated with each other to give a PA28γ$^{-/-}$ core Tg mouse. The PA28γ$^{-/-}$ core Tg was identified, according to the methods described in K. Moriya et al., J. Gen. Virol. 78, 1527 (1997), and S. Murata et al., J. Biol. Chem. 274, 38211 (1999), by PCR analysis of the PA28γ or HCV core gene as the target. Specifically, 1 μg of the genomic DNA extracted from mouse tail was amplified by PCR reaction using a synthetic oligonucleotide sense primer PA28-3 (SEQ. ID. No. 1) and an antisense primer PA28γ-5cr (SEQ. ID. No. 2), and the presence of the PA28γ gene (PA28γ$^{+/+}$) was confirmed by detecting the 0.75 kb amplified product. It is also amplified by PCR reaction using the sense primer PA28-3 (SEQ. ID. No. 1) and the PAKO-4 primer (SEQ. ID. No. 3), and presence of a mutant gene. PA28γ having a marker gene inserted, lacking the PA28γ gene (PA28γ$^{-/-}$), was confirmed by detecting the 0.90 kb amplified product. The HCV core protein was confirmed, according to the methods described in K. Moriya et al., J. Gen. Virol. 78, 1527 (1997), by PCR reaction and by detecting the 0.42 kb amplified product.

```
                                          SEQ. ID. No. 1:
5'-AGGTGGATCAGGAAGTGAAGCTCAA-3' (PA28-3)

SEQ. ID. No. 2:
5'-CACCTCACTTGTGATCCGCTCTCTGAAAGAATCAACC-3'
(PA28γ-5cr)

SEQ. ID. No. 3:
5'-TGCAGTTCATTCAGGGCACCGGACAG-3' (PAKO-4)
```

(3) Expression of mRNAs

FIG. 1b is an electrophoretic photograph of a PCR amplification product used in genotyping. In the present description, a wild-type mouse is called "PA28γ$^{+/+}$"; a core protein-transduced mouse, "core Tg" or "PA28γ$^{+/+}$ core Tg"; a mutant PA28γ mouse lacking the PA28γ gene, "PA28γ$^{-/-}$"; a core protein-transduced mouse lacking the PA28γ gene, "PA28γ$^{-/-}$ core Tg". The molecular weight and the expression level of the HCV core protein was similar between the PA28γ$^{-/-}$ core Tg mouse and the PA28γ$^{+/+}$ mouse. The expression level of PA28γ in the PA28γ$^{+/+}$ core Tg mouse was similar to that in the wild-type (PA28$^{+/+}$) mouse.

(4) Expression of Proteins

FIG. 1C is a Western blotting image for analysis of the proteins expressed in the mouse liver tissue. Specifically, the liver tissue of the 6 months old mice were subjected to SDS-PAGE, using its supernatant (200 μg-protein/lane) as sample, and then, to Western blotting analysis by using the HCV core protein, PA28γ, and the monoclonal antibody to β-actin. The mouse was processed according to the guideline, fed with CRF-1 (manufactured by Charles River Laboratories Japan Inc.) commercially available for feeding mice, and grown under special pathogenic microbe-free condition.

(5) Sex Difference

As for the body weight of the 6 months old mice, there was no significant difference among PA28γ$^{+/+}$, PA28γ$^{+/+}$ core Tg, PA28γ$^{-/-}$ core Tg, and PA28γ$^{-/-}$ mice, as shown in FIG. 1d. The amount of the core protein expressed in the liver of the PA28γ$^{+/+}$ core Tg and PA28γ$^{-/-}$ core Tg mice was determined by ELISA analysis (mean±S.D., n=10). As a result, the expression amount of the core protein was higher in male mice than in female mice, both in PA28γ$^{+/+}$ core Tg mice and PA28γ$^{-/-}$ core Tg mice, as shown in FIG. 1e.

(Evaluation Tests)

1. Tissue Staining

Mouse livers with various genotypes were fixed with formalin and embedded in paraffin by a conventional method, and expression of the HCV core protein in the frozen section thus prepared (formalin-fixed tissue section) was examined by the following method and stained with hematoxylin-eosin or oil red. The results are shown in FIGS. 2a to 2c.

Figure 2:
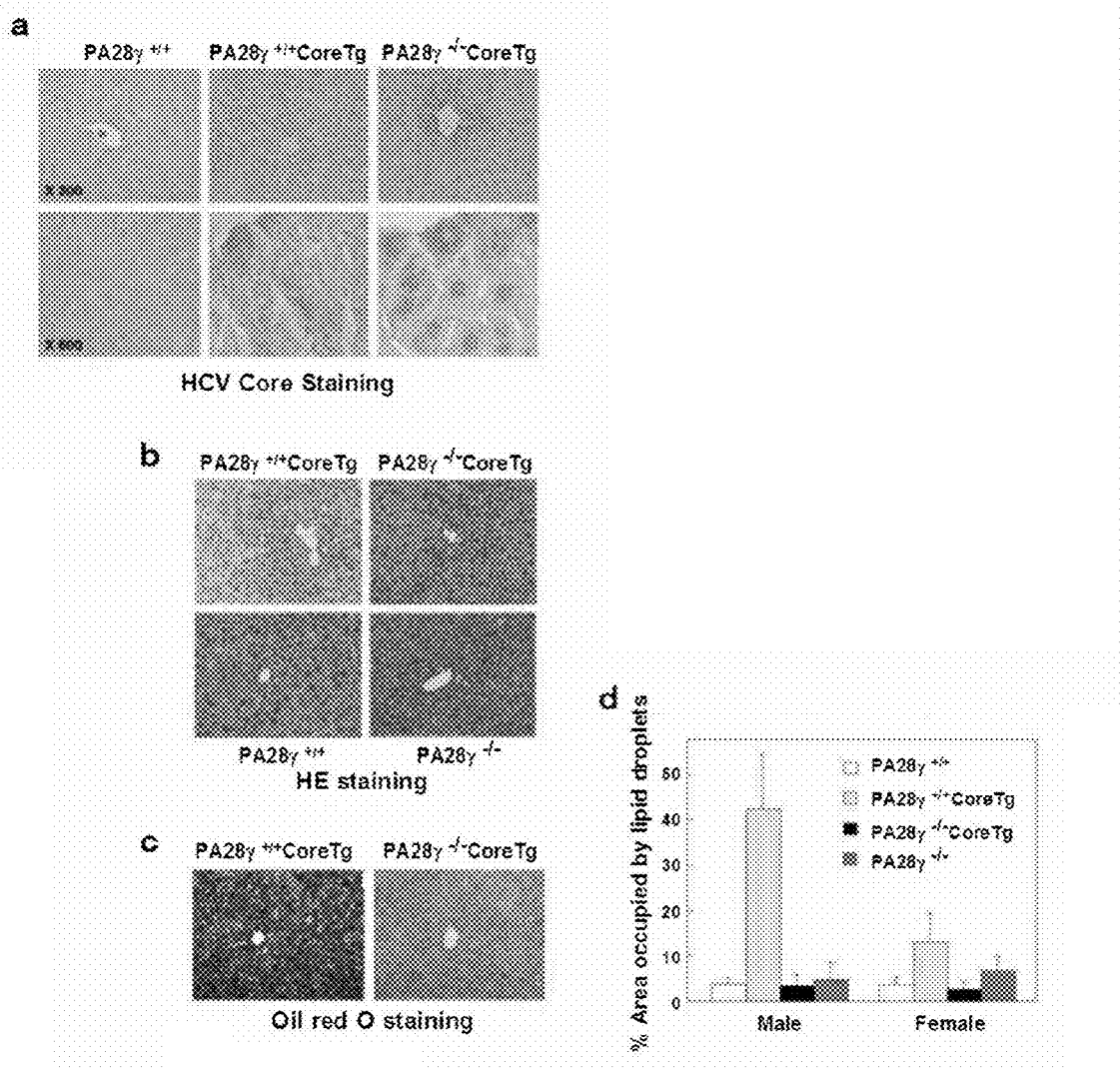
FIG. 2(a) shows tissue photographs of frozen mouse liver sections stained with an anti-HCV core protein antibody.
FIG. 2(b) shows tissue photographs stained with hematoxylin eosin.
FIG. 2(c) shows tissue photographs stained with oil red O.
FIG. 2(d) shows graphs which compare the staining areas stained with oil red O in the frozen liver sections of mice different in genotype and sex.

FIG. 2a is a photograph visualizing expression of the HCV core protein in three kinds of mouse liver sections with different genotype. Specifically, each of formalin-fixed tissue sections prepared from the livers of mice of 2 months of age, respectively having genotypes of PA28γ$^{+/+}$, PA28γ$^{+/+}$ core Tg, and PA28γ$^{-/-}$ core Tg was treated in 3% hydrogen peroxide solution, washed with phosphate buffer (PBS) twice, blocked with 5% bovine serum albumin-containing PBS, incubated with anti-HCV core protein rabbit antibody overnight, and incubated with the second antibody, horseradish peroxidase-bound anti-rabbit IgG antibody (ICN); and then, the immunoreactive antigen was visualized by using 3,3'-diaminobenzidine as substrate.

The results showed definite accumulation of the HCV core protein in the nucleus of the liver cell of PA28γ$^{-/-}$ core Tg mouse, clearly demonstrating that at least some fraction of the HCV core protein migrated into the nucleus and was decomposed therein via the PA28γ-dependent route.

FIG. 2b is a photograph showing the hematoxylin-eosin staining of two mouse liver sections with different genotype. Specifically, a formalin-fixed tissue section prepared with the liver collected from 6 months old mice having a genotype of PA28γ$^{+/+}$ core Tg or PA28γ$^{-/-}$ core Tg was stained with hematoxylin and eosin.

The results showed significant inhibition of vacuole formation in the PA28γ$^{+/+}$ core Tg mouse. It is generally known that gentle vacuole production is observed in the cytoplasm of the liver cell of 4 months old PA28γ$^{+/+}$ core Tg mouse and more rigorous production in the 6th month, but there was no inhibition of vacuole formation, similar to that in the PA28γ$^{+/+}$ core Tg mouse, in the 6 months old mice having the PA28γ$^{-/-}$ core Tg, PA28γ$^{+/+}$ and PA28γ$^{-/-}$ genotypes.

FIG. 2c is a photograph visualizing the results after the lipid accumulated in the liver sections of two kinds of mice different in genotype was stained with oil red O. Specifically, the formalin-fixed tissue sections prepared from the livers of mice of 6 months old mice having genotypes respectively of PA28γ$^{+/+}$ core Tg and PA28γ$^{-/-}$ core Tg were stained with oil red O.

The results suggested that the vacuole formation region in the PA28γ$^{+/+}$ core Tg mouse liver is stained definitely with oil red O, indicating development of severe adiposis in the core Tg mouse.

FIG. 2d is a graph showing the results of comparison, between male and female mice, of the areas containing lipid droplets accumulated in the liver sections of four kinds of mice different in genotype. Specifically, formalin-fixed tissue sections prepared from the livers of 6 months old mice having genotypes respectively of PA28γ$^{+/+}$, PA28γ$^{+/+}$ core Tg, PA28γ$^{-/-}$ core Tg, and PA28γ$^{-/-}$ were stained with oil red O, and the rate of the stained area occupied by lipid droplets (area ratio to the entire section area) was calculated by using Image-Pro software (product of Media Cybernetics Inc.). In the graph, the area occupied by lipid droplets (Y axis) was determined by measuring the size at three different sites in randomly selected 5 sections and calculating the average thereof form 10 samples for each genotype.

The results showed that the areas occupied by lipid droplets in the livers of PA28γ$^{+/+}$ core Tg male and female mice were respectively approximately 10 times and 2 to 4 times larger than those of wild-type male and female mice, indicating that PA28γ was essential in induction of fatty liver by the HCV core protein in mice.

2. Real-time PCR

Figure 3:
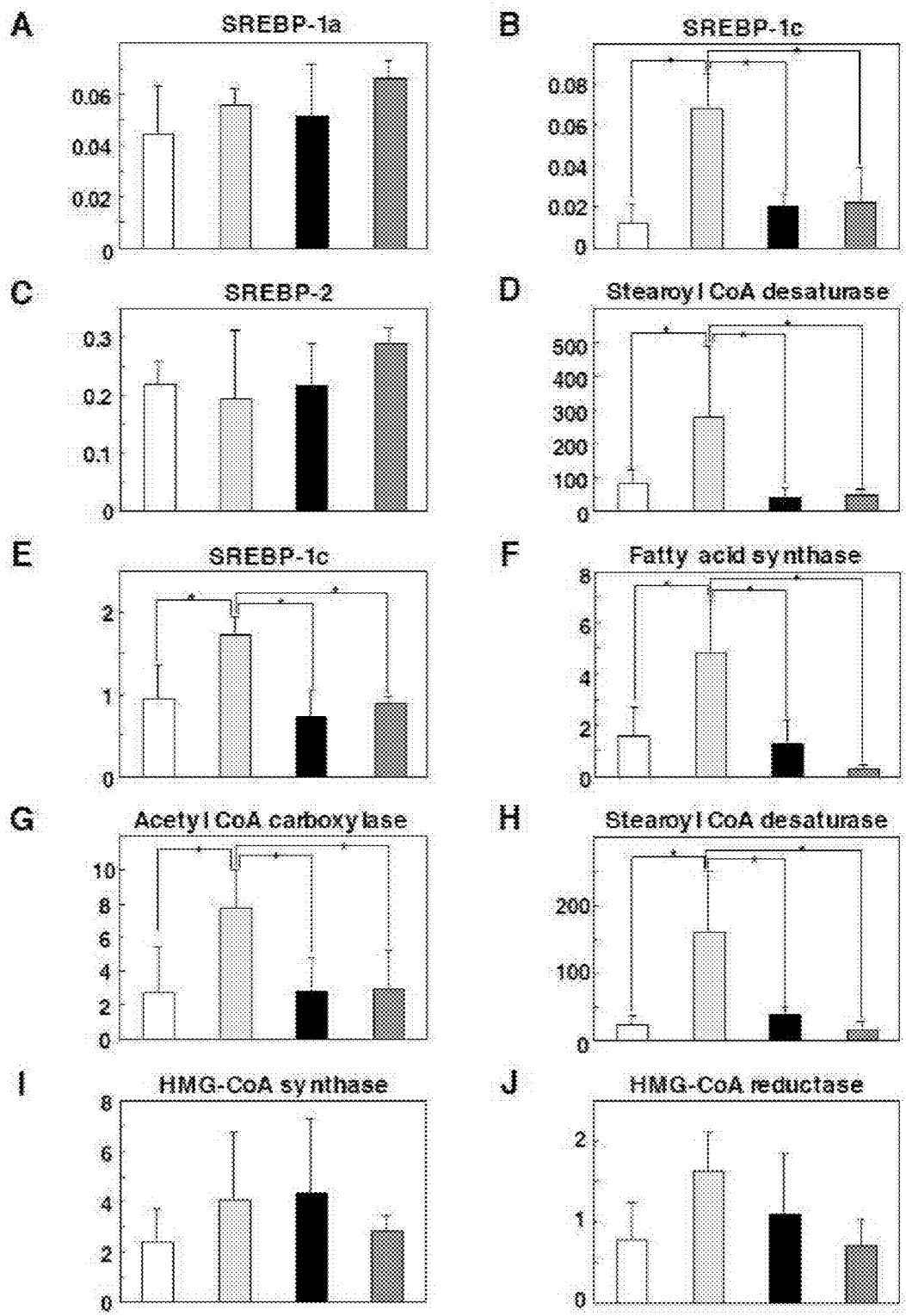
FIG. 3 is a graph showing the amounts of the lipid synthesis-control gene transcribed in 4 kinds of mouse livers different in genotype.

Transcription products of the lipid synthesis-control factors in the livers of four mice with different genotype were compared by the following method. The lipid synthesis-control factors used were SREBP-1a, SREBP-1c and SREBP-2 belonging to SREBP family, and also, acetyl CoA carboxylase producing saturated and monounsaturated fatty acids and triglyceride, fatty acid synthase and stearoyl CoA desaturase that are known to be controlled by the SREBP-1c. Total RNA wad prepared from each of the livers of 2 months or 6 months old mice respectively having genotypes of PA28γ$^{+/+}$, PA28γ$^{+/+}$ core Tg, PA28γ$^{-/-}$ core Tg, and PA28γ$^{-/-}$ by using Trizol LS (manufactured by Invitrogen Corporation). First Strand cDNA was synthesized by using First Strand cDNA synthesis kit (manufactured by Amersham Pharmacia Biotech). The amount of cDNAs in each sample was estimated by using Platinum SYBR Green pPCR Supermix UDG (manufactured by Invitrogen Corporation) according to the protocol attached therewith. The fluorescence signal was determined by using ABI Prism 7000 (manufactured by Applied Biosystems Japan). In the combination of the primers shown in Table 1, base sequences corresponding to SREBP-1a, SREBP-1c, SREBP-2, stearoyl CoA desaturase, acetyl CoA carboxylase, fatty acid synthase, HMG CoA reductase, HMG CoA synthase, and hypoxanthine-phosphoribosyltransferase (HPRT) were amplified. For prevention of pseudopositive amplification of impurity-containing genome DNAs, sense and antisense primers were located on different exons. Each PCR product was identified as a single band of accurate molecular weight by agarose gel electrophoresis.

the amounts of the genes transcripted in the mice respectively having genotypes of PA28γ$^{+/+}$, PA28γ$^{+/+}$ core Tg, PA28γ$^{-/-}$ core Tg, and PA28γ$^{-/-}$. FIG. 3 shows the relative values normalized with the HPRT corresponding to the amount of transcription of the genes coding SREBP-1a (A), SREBP-1c (B), SREBP-2 (C), and stearoyl CoA desaturase (D) in the livers of 2 months old mice, and also the transcription amount of the genes coding SREBP-1c (E), fatty acid synthase (F), acetyl CoA carboxylase (G), stearoyl CoA desaturase (H), HMG CoA reductase (I), and HMG CoA synthase (J) in the livers of 6 months old mice.

As shown in FIGS. 3A to 3D, transcription of SREBP-1c and the downstream stearoyl CoA desaturase was more activated in the livers of 2 months old PA28γ$^{+/+}$ core Tg mice than in mice of PA28γ$^{-/-}$ core Tg, PA28γ$^{+/+}$ and PA28γ$^{-/-}$, while there was no difference in transcription of SREBP-2 and SREBP-1a. In addition, as shown in FIGS. 3E to 3J, transcription of SREBP-1c and the enzymes under control thereof such as acetyl CoA carboxylase and fatty acid synthase as well as that of the stearoyl CoA desaturase was activated in the livers from 6 months old PA28γ$^{+/+}$ core Tg mice, compared to the livers from PA28γ$^{-/-}$ core Tg, PA28γ$^{+/+}$, and PA28γ$^{-/-}$ mice. In contrast, there was not statistically significant difference in transcription of the cholesterol biosynthesis-related genes (HMG CoA synthase and HMG CoA reductase) under control of SREBP-2. The results above suggest that both the HCV core protein and PA28γ are needed for activation of SREBP-1c transcription in mouse liver, and that even if the HCV core protein accumulates in the nucleus because it is not degraded by the PA28γ-dependent proteasome pathway (for example, in the case of PA28γ$^{+/+}$ core Tg mouse), and thus, there is no influence on the SREBP-1c promoter activity.

TABLE 1

| Genes | Sense primer | Antisense primer |
|---|---|---|
| SREBP-1a | SEQ. ID. No. 4<br>CACAGCGGTTTTGAACGACA | SEQ. ID. No. 5<br>CTGGCTCCTCTTTGATCCCA |
| SREBP-1c | SEQ. ID. No. 6<br>ACGGAGCCATGGATTGCACATTTG | SEQ. ID. No. 7<br>TACATCTTTAAAGCAGCGGGTGCCGATGGT |
| SREBP-2 | SEQ. ID. No. 8<br>ACCATTCTCCAGCAGTTCCGT | SEQ. ID. No. 9<br>CCTCTCACAGTGACAGAAGGAGTT |
| Stearoyl CoA desaturase | SEQ. ID. No. 10<br>TTCCCTCCTGCAAGCTCTAC | SEQ. ID. No. 11<br>CGCAAGAAGGTGCTAACGAAC |
| Acetyl CoA carboxylase | SEQ. ID. No. 12<br>GACAAACGAGTCTGGCTACT | SEQ. ID: No. 13<br>TGATGAGTGACTGCCGAAAC |
| Fatty acid synthase | SEQ. ID. No. 14<br>CTCCAAGACTGACTCGGCTACT | SEQ. ID. No. 15<br>AGCTGGGAGCACATCTCGAA |
| HMG CoA reductase | SEQ. ID. No. 16<br>GGTTGGAGTGTTCTCTTACGG | SEQ. ID. No. 17<br>CTCTGACCAGATACCACGTTC |
| HMG CoA synthase | SEQ. ID. No. 18<br>TATGCCCATCCCTGTTGGAG | SEQ.-ID. No. 19<br>CACGTGGAGTTTCTCTAGACGA |
| HPRT | SEQ. ID. No. 20<br>CCAGCAAGCTTGCAACCTTAACCA | SEQ. ID. No. 21<br>GTAATGATCAGTCAACGGGGAC |

The transcription amount of lipid synthesis-control genes, such as SREBP-1a, SREBP-1c, SREBP-2, stearoyl CoA desaturase, acetyl CoA carboxylase, fatty acid synthase, HMG CoA reductase, and HMG CoA synthase, was expressed as a numerical value normalized with the transcription amount of HPRT (n=5, *: 0.05>p, **: 0.01>p). Four bars in white, gray, black and dark gray in the graph of FIG. 3 show

3. Incidence Rate of Liver Cancer

Sixteen to 18 months old male and female mice having a genotype either of PA28γ$^{+/+}$ core Tg, PA28γ$^{+/-}$, PA28γ$^{-/-}$ or PA28γ$^{-/-}$ core Tg were analyzed for determination of the incidence rate of liver cancer. Specifically, the livers of each of the mice were dissected and examined whether it has liver cancer. The results are summarized in Table 2.

TABLE 2

| Genotype | Sex | Number of test mice | Number of mice with liver cancer | Incidence rate (%) |
|---|---|---|---|---|
| PA28γ$^{+/+}$ core Tg | male | 17 | 5 | 29.4 |
|  | female | 28 | 3 | 10.7 |
| PA28γ$^{+/-}$ | male | 16 | 0 | 0 |
|  | female | 4 | 0 | 0 |
| PA28γ$^{-/-}$ | male | 23 | 0 | 0 |
|  | female | 13 | 0 | 0 |
| PA28γ$^{-/-}$ core Tg | male | 15 | 0 | 0 |
|  | female | 21 | 0 | 0 |

The results showed that there was no incidence of liver cancer in all tested mice, male or female, having a genotype of PA28γ$^{+/-}$ mouse, PA28γ$^{-/-}$ mouse or PA28γ$^{-/-}$ core Tg mouse, while there were mice with liver cancer, both male and female, in the mice having a genotype of PA28γ$^{+/+}$ core Tg. Specifically, the incidence rate of liver cancer in of 16 to 18 months old male PA28γ$^{+/+}$ core Tg mice was 29.4% (5 in 17 mice), which was significantly higher than that of 10.7% (3 in 28 mice) of the female mice in the same age range. These results indicate that PA28γ plays a role essential for development of the HCV core protein-derived liver cancer.

Example 2

Activating Effect of SREBP-1c Promoter Activity by HCV Core Protein and PA28γ

Figure 4:
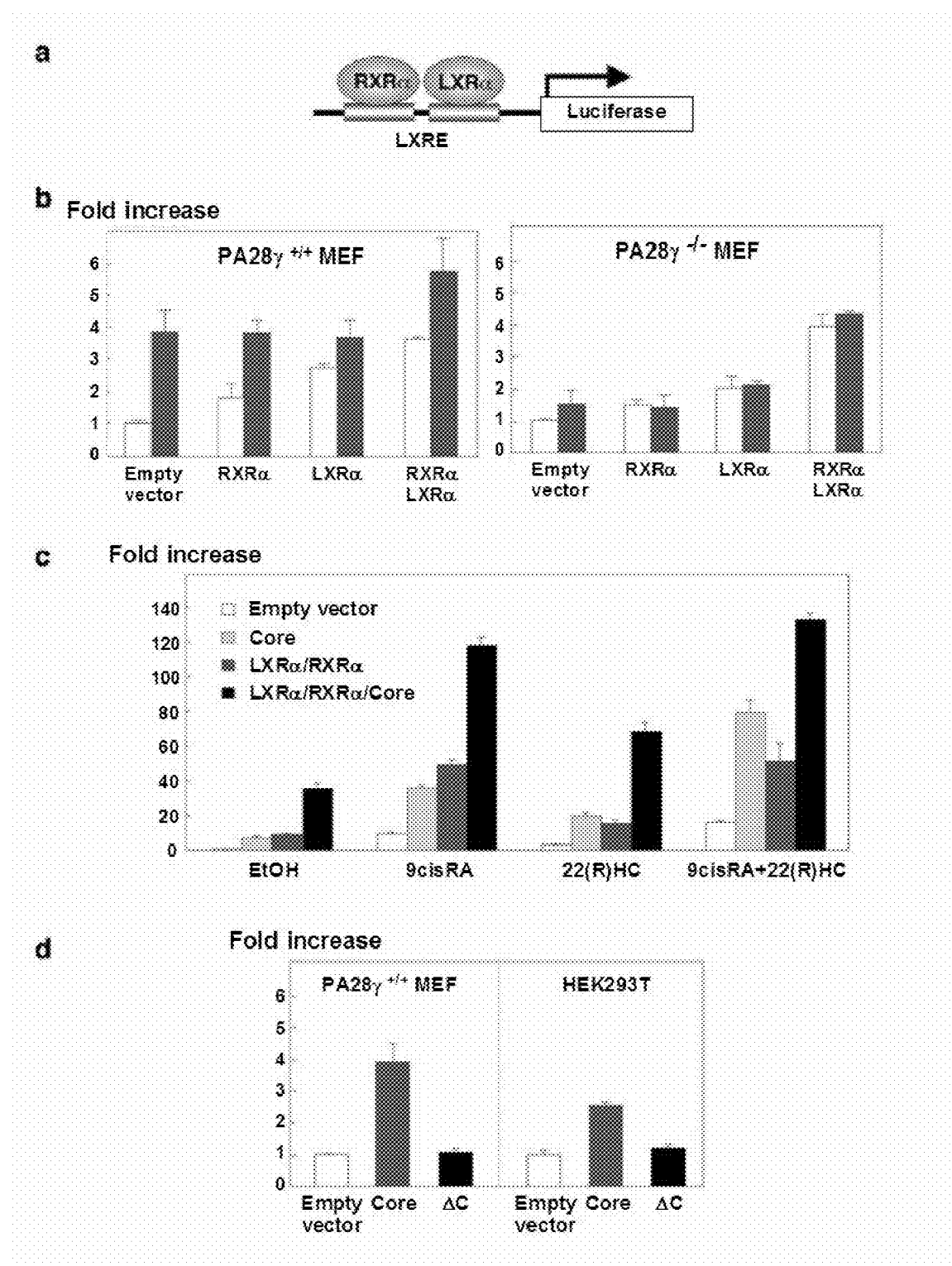
FIG. 4 shows the results of a reporter assay for evaluation of the influence on SREBP-1c promoter activity by HCV core protein and PA28γ.

A genome DNA fragment coding the SREBP-1c promoter region (located in residues −410 to +24 base region) from mouse genome was amplified, and the resulting fragment was inserted into KpnI and HindIII sites in pGL3-Basic (manufactured by Promega Corporation), to give pGL3-SREBP-1cPro (FIG. 4a).

(1) Measurement of SREBP-1c Promoter Activity by Using MEFs (FIG. 4b)

Mouse-derived embryonic fibroblasts (MEFs) respectively having genotypes of PA28γ$^{+/+}$ and PA28γ$^{-/-}$ were prepared by the method described in S. Murata et al., J. Biol. Chem. 274, 38211 (1999), and cultivated in a DMEM medium (manufactured by Sigma Corporation) containing 10% fetal calf serum, penicillin, streptomycin, pyruvate sodium, and non-essential amino acids under the atmosphere of a temperature of 37° C. and 5% carbon dioxide. Subsequently, PA28γ$^{+/+}$ MEFs or PA28γ$^{-/-}$ MEFs were transformed with the pGL3-srebp-1cPro and a control plasmid coding Renilla luciferase (manufactured by Promega) by using the plasmids in the following combinations. Specifically, the transformation was carried out by using any one of plasmids: (i) empty plasmid, (ii) only RXRα-coding plasmid, (iii) only LXRα-coding plasmid, and (iv) RXRα and LXRα-coding plasmid, and simultaneously by using (v) a plasmid coding the HCV core protein (white bar in the graph of FIG. 4b) or not using it (gray bar in the graph of FIG. 4b). The total amount of the DNA used in transfection was uniformized by adding the vacant plasmid. After cultivation for 24 hours, the cells were collected, and the luciferase activity of the cells was determined by using a dual luciferase reporter assay system (manufactured by Promega Corporation). The firefly luciferase activity was shown as the multiple of the Renilla luciferase activity (RLUs), which was used as the indicator. The results are shown in the graph of FIG. 4b. In FIG. 4b, the left graph shows the luciferase activity when the PA28γ$^{+/+}$ MEFs (left) were transformed with plasmids in combination of any one of plasmids (i) to (iv) and (V) a plasmid coding the HCV core protein (white bar), or with any plasmid (i) to (iv) above without addition of (V) (gray bar), while the right graph shows the same when the PA28γ$^{-/-}$ MEFs cells were treated similarly.

The results show that the activity of the SREBP-1c promoter was induced by endogenous expression of LXRα and RXRα in PA28γ$^{+/+}$ mouse embryonic fibroblasts (MEFs) expressing the HCV core protein (FIG. 4b, left). The SREBP-1c promoter activity by the HCV core protein was increased also by exogenous expression of LXRα and RXRα, in the MEFs of PA28γ$^{+/+}$ mouse. However, enhancement of the activation of the SREBP-1c promoter by the HCV core protein was not observed in the MEFs of PA28γ$^{-/-}$ mouse (FIG. 4b, right). These results are consistent with the in-vivo observation that both the HCV core protein and PA28γ are needed for enhancement of transcription of SREBP-1c.

(2) Measurement of SREBP-1c Promoter Activity by Using HEK293T Cells (FIG. 4c)

Human embryonic kidney cells (HEK293T: cell expressing endogenous PA2865) were transformed with the control plasmid coding pGL3-srebp-1cPro and Renilla luciferase (manufactured by Promega Corporation) and together with any one plasmid of (i) vacant plasmid, (ii) plasmid coding the HCV core protein, (iii) plasmid coding RXRα and LXRα, and (iv) plasmid coding RXRα, LXRα and the HCV core protein. The transformant obtained was cultivated in a culture solution containing a RXRα's ligand 9-cis-retinoic acid (9cisRA; product of Sigma Corporation), a LXRα's ligand 22(R)-hydroxycholesterol (22(R)HC), or both of them as additives for 24 hours, and then, the cells were collected; the luciferase activity of the cells was determined, similarly to (1) above, by using the dual luciferase reporter assay system (manufactured by Promega Corporation).

The results show that treatment of the HEK293T cell expressing endogenous LXRα and RXRα with the RXRα's ligand 9-cis-retinoic acid and/or the LXRα's ligand 22(R)-hydroxycholesterol leads to increase in SREBP-1c promoter activity by the HCV core protein. These results support the idea that the HCV core protein increases the SREBP-1c promoter activity, dependently on RXRα and LXRα.

(3) SREBP-1c Promoter Activity of Mutant HCV Core Protein (FIG. 4d)

For more information on increase in the SREBP-1c promoter induced by the HCV core protein, the activity of the mutant HCV core protein was studied by the following method:

A mutant of the HCV core protein lacking its C-terminal transmembrane region and ER anchor region (amino acid sequence: 174 to 191) was prepared. PA28γ$^{+/+}$ MEFs or 293T cells were transfected via liposome-mediated transfection with any one of the vacant plasmid, the plasmid coding the HCV core protein, and the plasmid coding the mutant core protein and using LipofectAMINE 2000 (manufactured by Invitrogen Corporation). The amount of the HCV core protein in liver tissue was determined by the ELISA method described in K. Aoyagi et al., J. Clin. Microbiol. 37, 1802 (1999). The cell supernatant was subjected to 12.5% SDS-PAGE, and the desired fractions were transferred onto a PDVF membrane. The proteins on the membrane were treated with a specific antibody and Super Signal Femto (manufactured by Pierce) and visualized by using LAS3000 imaging system (manufactured by Fuji Photo Film Co., Ltd.).

As a result, the mutant core protein lacking the C-terminal transmembrane region and the ER anchor region (amino acid sequence: 174 to 191) could not activate the SREBP-1c promoter activity both in PA28γ$^{+/+}$ MEFs and HEK293T cells (FIG. 4d). These results suggest that not only degradation of the HCV core protein in nucleus via the PA28γ-dependent pathway but also localization of the HCV core protein in cytoplasm are needed for in-vivo activation of the SREBP-1c promoter.

Example 3

Screening Using the Inhibitory Activity on the Interaction Between Core Protein and PA28γ as Indicator Human embryonic kidney cells (HEK293T) are transformed by using the combination of the pGL3-srebp-1cPro, a control plasmid coding *Renilla* luciferase (manufactured by Promega Corporation), and a plasmid coding RXRα, LXRα and the HCV core protein; and the resulting transformant is cultivated in a medium containing a RXRα's ligand 9-cis-retinoic acid (9cisRA; product of Sigma Corporation) and a LXRα's ligand 22(R)-hydroxycholesterol (22(R)HC) in the presence or absence of the test substance for 24 hours. The cells are then collected, and the luciferase activity thereof is determined by using a dual luciferase reporter assay system (manufactured by Promega).

The firefly luciferase activity is shown as the multiple of the *Renilla* luciferase activity (RLU), which is used as an indicator. The results show that the test substances showing significant difference in luciferase activity between in the presence and absence thereof are useful as prophylactic and/or therapeutic agents for HCV-related diseases.

Example 4

Prophylactic and/or Therapeutic Agents for HCV-related Diseases

A double-stranded oligo-RNA (siRNA) complementary to the partial sequence of the PA28γ mRNA was synthesized.

Human embryonic kidney cells (HEK293T) are transformed by using the combination of the pGL3-srebp-1cPro, the control plasmid coding *Renilla* luciferase (manufactured by Promega Corporation), and the plasmid coding RXRα, LXRα and the HCV core protein; the resulting transformant is cultivated in a medium containing the RXRα's ligand 9-cis-retinoic acid (9ciSRA; product of Sigma Corporation) and the LXRα's ligand 22(R)-hydroxycholesterol (22(R)HC) in the presence or absence of the siRNA for 24 hours. The cells are then collected, and the luciferase activity thereof is determined, similarly to the method in Example 3, by using a dual luciferase reporter assay system (manufactured by Promega Corporation), and the activity is expressed as the multiple of the RLUs. The results show that addition of siRNA leads to drastic decrease in luciferase activity, and thus, it is useful as a prophylactic and/or therapeutic agent for HCV-related diseases.

Industrial Applicability

According to the method of the present invention, it is possible, by examining the activity inhibiting interaction between the hepatitis C virus-derived core protein and the host-derived PA28γ, to efficiently identify a substance capable of controlling expression of lipid synthase through modification of transcriptional activity of such as lipid metabolism-control factors, as it is induced by the interaction. The substance thus obtained can be used as an active ingredient in lipid synthesis inhibitor, and, in particular, it is particularly useful as an active ingredient in prophylactic and/or therapeutic agent for prevention of development of diseases associated with hepatitis C such as fatty liver, liver cirrhosis and liver cancer and for suppressing progress of the symptoms thereof. The prophylactic and/or therapeutic agent according to the present invention may be administered therapeutically effectively to the patients with developed hepatitis C virus-related diseases and also to the HCV carrier patients before development of the diseases as a prophylactic agent for preventing development of the HCV-related diseases.

What is claimed is:

1. A screening method for identification of a lipid synthesis inhibitor agent useful for prevention and/or treatment of hepatitis C virus-related disease by indirectly determining if interaction between hepatitis C core protein and PA28γ protein is decreased by said agent, comprising the steps of:
   providing a cell that expresses HCV core protein, PA28γ, RXRα, and LXRα, and further expresses a reporter transcribed from a SREBP-c promoter;
   providing RXRα and LXRα ligands to the cell;
   exposing the cell to a test agent; and
   comparing the amount of transcription from the SREBP-c promoter in the presence and absence of the test agent;
   wherein a decrease in transcription in the presence of the test agent identifies the test agent as a lipid synthesis inhibitor agent.

* * * * *

SEQUENCE LISTING

```
<160> NUMBER OF SEQ ID NOS: 21

<210> SEQ ID NO 1
<211> LENGTH: 25
<212> TYPE: DNA
<213> ORGANISM: Artificial Sequence
<220> FEATURE:
<223> OTHER INFORMATION: sense primer PA28-3

<400> SEQUENCE: 1
aggtggatca ggaagtgaag ctcaa                                          25

<210> SEQ ID NO 2
<211> LENGTH: 37
<212> TYPE: DNA
<213> ORGANISM: Artificial Sequence
<220> FEATURE:
<223> OTHER INFORMATION: antisense primer PA28gamma-5cr

<400> SEQUENCE: 2
cacctcactt gtgatccgct ctctgaaaga atcaacc                             37

<210> SEQ ID NO 3
<211> LENGTH: 26
<212> TYPE: DNA
<213> ORGANISM: Artificial Sequence
```

```
<220> FEATURE:
<223> OTHER INFORMATION: PAKO-4 primer

<400> SEQUENCE: 3
tgcagttcat tcagggcacc ggacag                                    26

<210> SEQ ID NO 4
<211> LENGTH: 20
<212> TYPE: DNA
<213> ORGANISM: Artificial Sequence
<220> FEATURE:
<223> OTHER INFORMATION: SREBP-1a sense primer

<400> SEQUENCE: 4
cacagcggtt ttgaacgaca                                           20

<210> SEQ ID NO 5
<211> LENGTH: 20
<212> TYPE: DNA
<213> ORGANISM: Artificial Sequence
<220> FEATURE:
<223> OTHER INFORMATION: SREBP-1a antisense primer

<400> SEQUENCE: 5
ctggctcctc tttgatccca                                           20

<210> SEQ ID NO 6
<211> LENGTH: 24
<212> TYPE: DNA
<213> ORGANISM: Artificial Sequence
<220> FEATURE:
<223> OTHER INFORMATION: SREBP-1c sense primer

<400> SEQUENCE: 6
acggagccat ggattgcaca tttg                                      24

<210> SEQ ID NO 7
<211> LENGTH: 30
<212> TYPE: DNA
<213> ORGANISM: Artificial Sequence
<220> FEATURE:
<223> OTHER INFORMATION: SREBP-1c antisense primer

<400> SEQUENCE: 7
tacatcttta aagcagcggg tgccgatggt                                30

<210> SEQ ID NO 8
<211> LENGTH: 21
<212> TYPE: DNA
<213> ORGANISM: Artificial Sequence
<220> FEATURE:
<223> OTHER INFORMATION: SREBP-2 sense primer

<400> SEQUENCE: 8
accattctcc agcagttccg t                                         21

<210> SEQ ID NO 9
<211> LENGTH: 24
<212> TYPE: DNA
<213> ORGANISM: Artificial Sequence
<220> FEATURE:
<223> OTHER INFORMATION: SREBP-2 antisense primer

<400> SEQUENCE: 9
cctctcacag tgacagaagg agtt                                      24
```

```
<210> SEQ ID NO 10
<211> LENGTH: 20
<212> TYPE: DNA
<213> ORGANISM: Artificial Sequence
<220> FEATURE:
<223> OTHER INFORMATION: Stearoyl CoA desaturase sense primer

<400> SEQUENCE: 10
ttccctcctg caagctctac                                                   20

<210> SEQ ID NO 11
<211> LENGTH: 21
<212> TYPE: DNA
<213> ORGANISM: Artificial Sequence
<220> FEATURE:
<223> OTHER INFORMATION: Stearoyl CoA desaturase antisense primer

<400> SEQUENCE: 11
cgcaagaagg tgctaacgaa c                                                 21

<210> SEQ ID NO 12
<211> LENGTH: 20
<212> TYPE: DNA
<213> ORGANISM: Artificial Sequence
<220> FEATURE:
<223> OTHER INFORMATION: Acetyl CoA carboxylase sense primer

<400> SEQUENCE: 12
gacaaacgag tctggctact                                                   20

<210> SEQ ID NO 13
<211> LENGTH: 20
<212> TYPE: DNA
<213> ORGANISM: Artificial Sequence
<220> FEATURE:
<223> OTHER INFORMATION: Acetyl CoA carboxylase antisense primer

<400> SEQUENCE: 13
tgatgagtga ctgccgaaac                                                   20

<210> SEQ ID NO 14
<211> LENGTH: 22
<212> TYPE: DNA
<213> ORGANISM: Artificial Sequence
<220> FEATURE:
<223> OTHER INFORMATION: Fatty acid synthase sense primer

<400> SEQUENCE: 14
ctccaagact gactcggcta ct                                                22

<210> SEQ ID NO 15
<211> LENGTH: 20
<212> TYPE: DNA
<213> ORGANISM: Artificial Sequence
<220> FEATURE:
<223> OTHER INFORMATION: Fatty acid synthase antisense primer

<400> SEQUENCE: 15
agctgggagc acatctcgaa                                                   20

<210> SEQ ID NO 16
<211> LENGTH: 21
<212> TYPE: DNA
<213> ORGANISM: Artificial Sequence
<220> FEATURE:
<223> OTHER INFORMATION: HMG CoA synthase sense primer

<400> SEQUENCE: 16
```

```
ggttggagtg ttctcttacg g                                              21

<210> SEQ ID NO 17
<211> LENGTH: 21
<212> TYPE: DNA
<213> ORGANISM: Artificial Sequence
<220> FEATURE:
<223> OTHER INFORMATION: HMG CoA synthase antisense primer

<400> SEQUENCE: 17
ctctgaccag ataccacgtt c                                              21

<210> SEQ ID NO 18
<211> LENGTH: 20
<212> TYPE: DNA
<213> ORGANISM: Artificial Sequence
<220> FEATURE:
<223> OTHER INFORMATION: HMG CoA reductase sense primer

<400> SEQUENCE: 18
tatgcccatc cctgttggag                                                20

<210> SEQ ID NO 19
<211> LENGTH: 22
<212> TYPE: DNA
<213> ORGANISM: Artificial Sequence
<220> FEATURE:
<223> OTHER INFORMATION: HMG CoA reductase antisense primer

<400> SEQUENCE: 19
cacgtggagt ttctgtagac ga                                             22

<210> SEQ ID NO 20
<211> LENGTH: 24
<212> TYPE: DNA
<213> ORGANISM: Artificial Sequence
<220> FEATURE:
<223> OTHER INFORMATION: HPRT sense primer

<400> SEQUENCE: 20
ccagcaagct tgcaacctta acca                                           24

<210> SEQ ID NO 21
<211> LENGTH: 23
<212> TYPE: DNA
<213> ORGANISM: Artificial Sequence
<220> FEATURE:
<223> OTHER INFORMATION: HPRT antisense primer

<400> SEQUENCE: 21
gtaatgatca gtcaacgggg gac                                            23
```